United States Patent [19]

Caspari

[11] 4,137,183
[45] Jan. 30, 1979

[54] HYDROCARBYL TITANATE DITHIOPHOSPHATE COMPOSITIONS AND PROCESSES

[75] Inventor: Guntar Caspari, Wheaton, Ill.

[73] Assignee: Standard Oil Company (Indiana), Chicago, Ill.

[21] Appl. No.: 853,130

[22] Filed: Nov. 21, 1977

[51] Int. Cl.² ........................ C10M 1/48; C10M 3/42; C10M 5/24; C07F 7/28
[52] U.S. Cl. ........................... 252/32.7 E; 262/400 A; 260/429.5
[58] Field of Search ............... 252/32.7 E, 400 A; 260/429.5

[56] References Cited

U.S. PATENT DOCUMENTS

| 3,242,081 | 3/1966 | McHugh et al. | 252/32.7 E |
| 3,984,448 | 10/1976 | Lippemier | 260/429.5 |
| 4,083,860 | 4/1978 | Ruf | 260/429.5 |

*Primary Examiner*—Irving Vaughn
*Attorney, Agent, or Firm*—Mark J. DiPietro; Arthur G. Gilkes; William T. McClain

[57] ABSTRACT

A compound having the structure

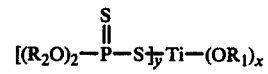

wherein $x+y=4$ and x ranges from 1 to 3 and y ranges from 1 to 3 and $R_1$ comprises a hydrocarbyl group of about 1 to about 18 carbon atoms and $R_2$ is a hydrocarbyl group of about 1 to 24 carbon atoms.

13 Claims, No Drawings

HYDROCARBYL TITANATE DITHIOPHOSPHATE COMPOSITIONS AND PROCESSES

This invention relates to hydrocarbyl titanate dithiophosphate lubricant additives. More particularly, this invention relates to the reaction product of tetra hydrocarbyl titanate or mixed hydrocarbyl titanate halide with a dihydrocarbyldithiophosphoric acid compound.

There has been considerable interest in recent years in new lubricant oil additive compositions. Many of these new additive compositions are based on titanium compounds. U.S. Pat. No. 3,984,448 discloses the production of metal salts of dialkyldithiophosphate in which the metal salt can be provided by titanium oxide. U.S. Pat. No. 3,242,081 discloses compositions consisting of a base oil of lubricating viscosity and pi-bonded organo titanium salts having univalent carbocyclic radical pi-bonded to the titanium and an ion containing at least one element selected from the class consisting of sulfur and chlorine in an amount at least sufficient to improve the lubricating characteristics of said oil. Many of these compounds contain ionic bonds which limit solubility in oil. These compounds have the drawback that they do not enhance both the anti-wear and anti-oxidant property of the oils and are relatively expensive. Accordingly, there is a need for a new class of titanium compound capable of enhancing lubricant's properties.

The general object of the invention is to provide a new additive composition and lubricant oil composition. Another object of the composition is to provide lubricating oil compositions having improved anti-wear and anti-oxidant properties. It is a further object of the invention to provide lubricating oil composition having multi-functional properties such as dispersancy, anti-oxidant properties, anti-wear and load-bearing properties.

I have now found that hydrocarbyl titanate dithiophosphates constitute a new class of additive suitable for use as lubricant oil additives. These compounds consist of covalently bonded quadrivalent titanium derivatives in which the substituents on the titanium are either alkoxy, aroxy, alkaroxy substituents or dithiophosphate substituents. Lubricating oil compositions containing hydrocarbyl titanate dithiophosphate additives derive anti-wear properties from the hydrocarbyl titanate moiety and anti-oxidant properties from the dithiophosphate moiety.

The compounds of this invention can be represented by the following structural formula:

$$(R_1O)_x Ti-[S-\overset{\overset{S}{\|}}{P}-(OR_2)_2]_y \qquad (I)$$

Briefly, the hydrocarbyl titanate dithiophosphate compounds can be prepared by reacting a tetra hydrocarbyl titanate compound or mixed hydrocarbyl titanium halide, with a dihydrocarbylphosphoric acid compound. The equations II and III are examples of the reactions producing the above compound.

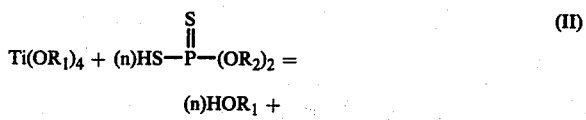

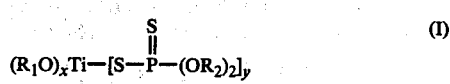

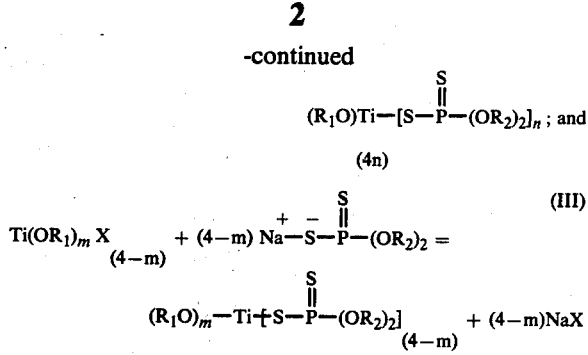

In equations I, II, and III m, n, x and y are numbers from 1 to 3, $x + y = 4$, $R_1$ is an alkyl, aryl, or alkaryl group of about 1 to 18 carbon atoms $R_2$ is a hydrocarbyl group of about 1 to 24 carbon atoms and X is a halide (chloro, bromo, etc.) atom. The number of hydrocarbyl and dihydrocarbyldithiophosphate substituents on the titanium can be altered by changing the reactant molar ratios.

"Chemistry and Uses of Titanium Organic Compounds" by John H. Haslam, Volume 23, *Metal Organic Compounds*, Advances in Chemistry Series, published by the American Chemical Society, pages 272–281 teach reactions for making tetra hydrocarbyl titanate compounds and hydrocabyl titanate halide compounds.

The $R_1$ substituent of the tetra hydrocarbyl titanate compounds can be methyl, ethyl, propyl, isopropyl, butyl, isobutyl, t-butyl, n-octyl, 2-ethylhexyl, dodecyl, octadecyl or an alkyl phenyl group the alkyl group having about 1 to 12 carbon atoms such as phenyl, p-methyl phenyl, 2,6-dit-butyl phenyl, dodecyl phenyl, and mixtures thereof, etc.

The hydrocarbyl group of the dihydrocarbyl dithiophosphate comprise groups containing about 1 to 24 carbon atoms. Examples of these alkyl and alkenyl groups are methyl, ethyl, vinyl, propyl, isopropyl, butyl, isobutyl, t-butyl, amyl, hexyl, cyclohexyl, methyl cyclohexyl, heptyl, octyl, 2-methyl-1-pentyl, 2,2-dimethyl-1-octanyl, 2-ethylhexyl, nonyl, decyl, dodecyl, undecyl, tetracosyl, or an alkyl phenyl group, the alkyl having about 1 to 18 carbon atoms, phenyl, alkylphenyl such as nonyl phenyl, dodecylphenyl, methylphenyl, dimethylpenyl, other substituted phenyls and mixtures thereof.

Salts of the dihydrocarbyldithiophosphoric acid such as the salts used in equation III can be prepared by the addition of ammonium hydroxide or a group (I) hydroxide or a group (II) metal oxide or hydroxide to a solution of the dihydrophosphoric acid. The neutralization occurs readily and the resulting salts are commonly oil soluble. The preferred neutralizing agents are ammonium, sodium or potassium hydroxide. The reaction mixture is commonly heated to remove water of neutralization.

In somewhat greater detail hydrocarbyl titanate dithiophosphate compounds are prepared by the reaction of a dihydrocarbyldithiophosphoric acid compound and a tetra hydrocarbyl titanate or a mixed hydrocarbyl titanate halide.

The reaction commonly can be carried out by adding the dihydrocarbyldithiophosphate to the tetra hydrocarbyl titanate dissolved in solvent. Alternatively, the soluble dihydrocarbyldithiophosphate salt can be added to mixed hydrocarbyl titanate halide in solvent solution. The reactions proceed readily at room temperature or at elevated temperature. Preferably the reactions are carried out at a temperature from about 10° C. to about 200° C., most preferably from 50° C. to 100° C. These reaction temperatures are preferred due to the rapid rates of reactions and low amount of degradation of reaction reactants. The reactions are commonly carried out for a period of time from about 1 minute to about 10 hours, preferably, about 10 minutes to about 2 hours depending upon the temperature and the substituents on the titanium and the dihydrocarbyldithiophosphate compounds. The reaction is generally complete within about 2 hours. The mole ratios of titanium compound to dihydrocarbyldithiophosphate compound can range from about 1:4.0–1.0 preferably about 1:2.0–1.0 to produce titanium compounds of highest anti-wear and anti-oxidant activity.

The hydrocarbyl titanate dithiophosphate can be prepared in batch or continuous processes. In batch processes, the solvent solution of reactant or the reactant without solvent may be added to the other reactant in a suitable vessel. In continuous processing the two components in solution or solvent can be charged to different (countercurrent process) or the same reaction zone, e.g., the upper end of a vertical zone maintained at a suitable elevated temperature. The product commonly is withdrawn from the other end into purification strippers and filters.

At the conclusion of the reaction, little purification need be done to the product and the reaction between the tetra hydrocarbyl titanate and the dihydrocarbyldithiophosphate acid. However, alcohol displaced from the titanium compound must be removed and insolubles when formed must also be removed. In the reaction between the mixed hydrocarbyl titanate halide and the salt of the dihydrocarbyldithiophosphoric acid, the halide salt produced by the displacement of the halide from the titanium compound and the cation from the salt must be removed, for example, by filtration from the reaction mixture.

The reactions producing the hydrocarbyl titanate dithiophosphate compositions are commonly carried out without a solvent or in a solvent inert to the reactants. The reaction may be carried out in lubricating oil. When carried out in lubricating oil, the additive composition is immediately ready to be blended to lubricating oils. Other solvents in which the reaction may be carried out are paraffins, chlorinated paraffins, ethers, aromatics, and others. Preferred solvents include hexane, heptane, diethyl ether, petroleum ether, toluene, benzene and xylenes.

The titanium composition of this invention are useful as lube oil additives in various oils such as synthetic, animal, vegetable or mineral oils. Ordinary mineral lubricating oils are usually preferred by reason of their availability, general excellence, and low cost. However, for certain applications, other oils are preferred. For instance, synthetic polyester oils are often preferred lubricants. Normally the lubricant oils are fluid oils, the viscosity of which is greater than 4.0 Saybolt Universal seconds at 210° F., preferably greater than 40 Saybolt Universal seconds at 210° F. This invention also contemplates the presence of other additives and lubricating compositions. Such additives include, for example, viscosity index improving agents, pour point depressing agents, anti-foam agents, extreme pressure agents, rust-inhibiting agents, and oxidation and corrosion inhibiting agents. The additive of this invention is generally added to lubricating oils in order to improve the anti-wear, load bearing, and anti-oxidant properties of said oil.

Depending on the nature of the oil and the intended use thereof and the intended environment, different amounts of the additive are needed in order to be effective. Generally, about 0.1 to about 10 weight percent, preferably from about 0.5 to about 2 weight percent of the additive is used in the oil.

EXAMPLE I

Thirty-four grams tetraisobutyl titanate (0.1 mole) was dissolved in 100 milliliters of toluene at 60° C. in a 3 necked 250 ml. flask equipped with a reflux condenser, dropping funnel and a stirrer. To this solution 75 grams of dinonylphenyl dithiophosphoric (0.1 mole) acid was added dropwise. After the addition the temperature was raised to 100° C. The reactions continued for 15 minutes and the solvent and generated isobutyl alcohol was removed by blowing the mixture with nitrogen. The reaction yielded 85 grams of a dark red oil. An analysis of the product showed that it contained 4.86% titanium, 2.72% phosphorus, and 7.05% sulfur.

EXAMPLE II

Example I was repeated except that 0.1 mole of dinonylphenyl dithiophosphoric acid and 0.1 mole of tetraisooctyl titanate were used. The reaction product yielded 6.93% titanium, 4.8% phosphorus, and 9.05% sulfur.

EXAMPLE III

Example I was reproduced except that 0.1 mole of dinonylphenyl dithiophosphoric was used with 0.1 mole of tetraisopropyltitanate. The reaction yielded a product that was 4.8% titanium, 3.7% phosphorus, and 7.1% sulfur.

EXAMPLE IV

Example I was repeated except that 0.1 moles of diisooctyloctyl dithiophosphoric acid and tetraisopropyl titanate were used. The reaction product was 6.7% titanium, 6.08% phosphorus, and 9.8% sulfur.

EXAMPLE V

Example I was repeated except that 0.1 mole of a mixed dialkyldithiophosphoric acid, which was prepared from a mixture of isobutanol, isoamyl alcohol and isooctanol was used with 0.1 moles of tetraoxypropyltitanate. The reaction yielded a compound whose composition is 6.24% titanium, 4.28% phosphorus, and 7.3% sulfur.

EXAMPLE VI

Example I was repeated except that 0.1 moles of diisoamyldithiophosphoric acid and 0.1 moles of tetra-2-ethylhexyl titanate were used. The reaction yielded a compound whose composition is 8.01% titanium, 6.40% phosphorus, and 11.5% sulfur.

TABLE I

TEST OIL FORMULATIONS*

| TEST COMPOSITIONS | Oil 5W (%) | Oil 10W (%) | Dispersant (%) | VI Improver (%) | Magnesium Sulfonate (%) | Alkoxy-titanium dithio phosphate from Example at (%) |
|---|---|---|---|---|---|---|
| 1 | 40 | 47 | 5 | 6 | 1 | I at 1.0% |
| 2 | 40 | 47 | 5 | 6 | 1 | II at 1.0% |
| 3 | 40 | 47 | 5 | 6 | 1 | III at 1.0% |
| 4 | 40 | 47 | 5 | 6 | 1 | IV at 1.0% |
| 5 | 40 | 47 | 5 | 6 | 1 | V at 1.0% |

TABLE I-continued
TEST OIL FORMULATIONS*

| TEST COMPOSITIONS | Oil 5W (%) | Oil 10W (%) | Dispersant (%) | VI Improver (%) | Magnesium Sulfonate (%) | Alkoxy-titanium dithio phosphate from Example at (%) |
|---|---|---|---|---|---|---|
| 6  | 40 | 47 | 5 | 6 | 1 | VI at 1.0% |
| 7  | 99 |    |   |   |   | I at 1.0% |
| 8  | 99 |    |   |   |   | II at 1.0% |
| 9  | 99 |    |   |   |   | III at 1.0% |
| 10 | 99 |    |   |   |   | IV at 1.0% |
| 11 | 99 |    |   |   |   | V at 1.0% |
| 12 | 99 |    |   |   |   | VI at 1.0% |
| 13 | 40 | 46 | 5 | 6 | 1 | I at 2.0% |
| 14 | 40 | 46 | 5 | 6 | 1 | II at 2.0% |
| 15 | 40 | 46 | 5 | 6 | 1 | III at 2.0% |
| 16 | 40 | 46 | 5 | 6 | 1 | IV at 2.0% |
| 17 | 40 | 46 | 5 | 6 | 1 | V at 2.0% |
| 18 | 40 | 46 | 5 | 6 | 1 | VI at 2.0% |
| 19 | 40 | 48 | 5 | 6 | 1 | —at 0% |
| 20 | 100 |   |   |   |   | —at 0% |

*(%) in weight percent based on the oil.

The dispersant is a Mannich base made from polyisobutyl phenol, formaldehyde, and a tetraethylene pentamine; the VI improver is a high molecular weight polyester made from methacrylic acid and a long chain alcohol; the Magnesium Sulfonate is a polypropyl benzene sulfonate, overbased with MgO to a (TBN) total base number of 400.

Many variations from the examples and illustrations found above are possible. The examples and illustrations shown are to describe specific compositions which were prepared. Those skilled in the art will be able to create many other variations similar to those examples found above.

TABLE II
ANTI-OXIDENT-OIL THICKENING TEST

| TEST COMPOSITION | Time to Original Viscosity X4 (4V$_o$) (Hrs) | Dispersancy at 65 Hours (%) |
|---|---|---|
| 1  | 85  | 55  |
| 2  | 128 | 88  |
| 3  | 167 | 100 |
| 4  | 141 | 90  |
| 5  | 146 | 95  |
| 13 | 195 | 100 |
| 14 | 250 | 100 |
| 15 | 224 | 100 |
| 16 | 137 | 90  |
| 17 | 256 | 100 |
| 18 | 299 | 100 |
| 19 | 44  | 0   |

Anti-oxidative properties of oil composition were measured by an oil thickening test. In this test 100 grams of test oil are oxidized at 280° F. in an open oxidation tube, while being blown with 60 cc air/minute. Oxidation is catalyzed by the addition of metal wire. Samples are taken periodically and their viscosity determined to give a viscosity-time curve. The time in hours for a four-fold increase in viscosity over the initial viscosity (4VO) is noted; a long 4 VO indicates resistance to oil thickening by oxidation. Also. a sample of this oil after 48 hours of oxidation is run in the Spot Dispersancy Test which gives a measure of the oil's ability to disperse sludge and varnish. In the Spot Dispersancy Test, 3-10 drops of oil are dropped onto a standard white blotter paper on which is a sludge spot. The paper with sludge has been incubated for 24 hours at 210° F. After 24 hours, the diameter of the sludge spot and the oil spot are measured. Dispersancy is the ability of an oil to keep sludge in suspension. Thus, dispersancy will be reflected by the difference in diameters of the sludge and oil spots. A rating (SDT Rating) is given by the diameter of the sludge spot divided by the diameter of the oil spot, and multiplied by 100. A high numerical rating indicates good dispersancy.

TABLE III
LOAD BEARING-ANTI-WEAR

| TEST COMPOSITION | Four Ball Test** 30 Kg | ASTM-2266 WEAR SCAR DIAMETER (mm) 50 Kg |
|---|---|---|
| 7  | 0.41 | 0.90 |
| 8  | 0.48 | 0.90 |
| 9  | 0.40 | 0.82 |
| 10 | 0.55 | 0.81 |
| 11 | 0.56 | 1.00 |
| 12 | 0.47 | 0.90 |
| 20 (no additive) | greater than 2mm at 1 min. | — |

**Test Conditions: 1800 rpm; 0.5 hours.

ASTM-2266 is a test which determines the load-bearing properties of lubricating fluids. The testing machine is operated with one steel ball rotating against three steel balls held stationary to form a cradle. The balls are rotated at about 1770 ± 60 rpm at 65° to 95° F. at a certain kg-load. The test results in Tables show acceptable dispersancy, anti-oxidation, and load bearing properties.

I claim:

1. A compound having the structure

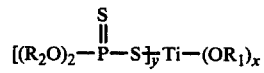

wherein x + y = 4 and x ranges from 1 to 3 and y ranges from 1 to 3 and R$_1$ comprises a hydrocarbyl group of about 1 to about 18 carbon atoms and R$_2$ is a hydrocarbyl group of about 1 to 24 carbon atoms.

2. The compound of claim 1 wherein R$_2$ comprises an alkyl phenyl group in which the alkyl has about 1 to 18 carbon atoms.

3. The compound of claim 1 wherein R$_1$ comprises an alkyl phenyl group wherein the alkyl group has about 1 to 12 carbon atoms.

4. A process for making hydrocarbyl titanate dithiophosphates comprising reacting a dihydrocarbyl dithiophosphoric acid compound and a titanium compound selected from the group consisting of tetra hydrocarbyl titanate compounds and mixed hydrocarbyl titanate halide compounds.

5. The process of claim 4 wherein the reaction comprises a tetra hydrocarbyl titanate and a hydrocarbyl dithiophosphoric acid.

6. The process of claim 4 wherein the reaction comprises a mixed hydrocarbyl titanate halide and a salt of a dihydrocarbyldithiophosphoric acid.

7. The process of claim 6 wherein the salt of the dihydrocarbyl dithiophosphate is selected from the group consisting of ammonium, alkali metal and alkali metal earth salts.

8. The process of claim 4 wherein the molar ratio of the hydrocarbyl titanate compound to the dihydrocarbyldithiophosphoric acid composition is about 1:4.0-0.1.

9. The process of claim 4 wherein the molar ratio of the hydrocarbyl titanate compound to the dihydrocarbyl dithiophosphoric acid compound is 1:2.0-1.0.

10. A lubricant comprising a major portion of a lubricant oil and an effective amount of the product of the process of claim 4.

11. The lubricant of claim 10 wherein the product of the process of claim 4 is present in the oil at about 0.1 to 10.0 percent by weight.

12. A lubricant comprising a major portion of a lubricant oil and an effective amount of the compound of claim 1.

13. The lubricant of claim 12 wherein the compound of claim 1 is present in the oil at about 0.1 to about 10.0 percent by weight.

* * * * *